US010376211B2

(12) United States Patent
Fuh et al.

(10) Patent No.: US 10,376,211 B2
(45) Date of Patent: Aug. 13, 2019

(54) METHOD FOR CONTINUOUSLY DETECTING BODY PHYSIOLOGICAL INFORMATION TRAJECTORIES AND ESTABLISHING DISEASE PREVENTION USING A PERSONAL WEARABLE DEVICE

(71) Applicants: Jean Fuh, New York, NY (US); Pei Chin Chen, Taipei (TW); Martin M. T. Fuh, Taipei (TW)

(72) Inventors: Jean Fuh, New York, NY (US); Pei Chin Chen, Taipei (TW); Martin M. T. Fuh, Taipei (TW)

(*) Notice: Subject to any disclaimer, the term of this patent is extended or adjusted under 35 U.S.C. 154(b) by 104 days.

(21) Appl. No.: 15/336,393

(22) Filed: Oct. 27, 2016

(65) Prior Publication Data

US 2017/0119308 A1 May 4, 2017

(30) Foreign Application Priority Data

Oct. 29, 2015 (TW) .............................. 104135668 A (51) Int. Cl.
*A61B 5/02* (2006.01)
*A61B 5/00* (2006.01)
(Continued)

(52) U.S. Cl.
CPC ............ *A61B 5/681* (2013.01); *A61B 5/0022* (2013.01); *A61B 5/021* (2013.01); *A61B 5/029* (2013.01); *A61B 5/02438* (2013.01); *A61B 5/0816* (2013.01); *A61B 5/14542* (2013.01); *A61B 5/7275* (2013.01); *A61B 5/742* (2013.01); *A61B 5/746* (2013.01); *A61B 5/7435* (2013.01); *A61B 5/7475* (2013.01); *G16H 50/30* (2018.01)

(58) Field of Classification Search
CPC .......... A61B 5/00; A61B 5/021; A61B 5/024; A61B 5/029; A61B 5/08; A61B 5/145; A61B 5/0022; A61B 5/742; A61B 5/7275; A61B 5/681; A61B 5/746; A61B 5/0816; A61B 5/02438; A61B 5/14542; A61B 5/7435; A61B 5/7475
See application file for complete search history.

(56) References Cited

U.S. PATENT DOCUMENTS

| | | | | |
|---|---|---|---|---|
| 5,316,008 A | * | 5/1994 | Suga ................... | A61B 5/02125 600/503 |
| 2016/0302735 A1 | * | 10/2016 | Noguchi .............. | A61B 5/6898 |
| 2018/0085011 A1 | * | 3/2018 | Ma ..................... | A61B 5/02125 |

* cited by examiner

*Primary Examiner* — Eric J Messersmith
(74) *Attorney, Agent, or Firm* — Dorsey & Whitney LLP

(57) ABSTRACT

A method for continuously detecting body physiological information trajectories through the use of a personal wearable device. Through short-distance wireless transmission, a smartphone or a computer first transmits basic information, including a personal ID of a user of the device, a device ID, an ID of the smartphone or the computer, and communication links, to a remote medical data center. In this case, the device continuously detects body physiological information which can be transmitted to the remote medical data center. Corrective body physiological information data of the user is measured and transmitted to the remote medical data center. The remote medical data center processes the data and periodic pulse volume curves. The remote medical data center then transmits the numeral data converted from periodic pulse volume curves back to the personal wearable device and continuously constructs a periodic trajectory of detected personal body physiological information.

3 Claims, 5 Drawing Sheets

(51) Int. Cl.
*A61B 5/021* (2006.01)
*A61B 5/024* (2006.01)
*A61B 5/029* (2006.01)
*A61B 5/08* (2006.01)
*A61B 5/145* (2006.01)
*G16H 50/30* (2018.01)

METHOD FOR CONTINUOUSLY DETECTING BODY PHYSIOLOGICAL INFORMATION TRAJECTORIES AND ESTABLISHING DISEASE PREVENTION USING A PERSONAL WEARABLE DEVICE

CROSS-REFERENCE TO RELATED APPLICATION

This application claims the benefit under 35 U.S.C. § 119 of the earlier filing date of Taiwanese Patent Application No. 104135668, filed Oct. 29, 2015, which application is incorporated by reference herein in its entirety and for all purposes.

TECHNICAL FIELD

A method for continuously detecting body physiological information trajectories and establishing disease prevention and cure through the use of a personal wearable device is provided. The method relates to the following technical fields: modern photoelectric technology, communication technology, information technology and medical technology, which are combined to execute continuous detection of body physiological information trajectories using a personal wearable device. Detection of body physiological information is implemented by using the photoelectric technology such as an infrared technology, a Nanosecond Pulse Near-field Sensing technology, or an Ultra Wide Band non-contact monitoring technology amongst electromagnetic wave technologies. Periodic pulse volume curves of body physiological information of a user are detected continuously, and by using the communication technology, the periodic pulse volume curves, numeral data, datum, and pictures about the body physiological information acquired through continuous detection are wirelessly transmitted to a smartphone or a computer via Bluetooth, and further forwarded to a remote medical data center. Then, professional healthcare measurement personnel can measure, by using a government approved device of the same type, body physiological information data of the user of the device for multiple times. The measured data is entered into the smartphone or the computer and then transmitted to a software program of the remote medical data center. In this case, the medical data center stores two types of body physiological information as described above. The software program using information technology will automatically extract body physiological information of two different forms within a same period of time, and carry out conversion, comparison, correction, analysis, calculation, processing and then storage. Then, a corrective physiological information value of a user in a real situation can be generated and early disease detection and prevention or continuous disease monitoring can be carried out by using modern medical technology. In addition, if required, the user of the personal wearable device may have personal physiological information value stored in the remote medical data center transmitted back to a screen (display) of the smartphone or the computer of the user for display, and then the personal physiological information value is forwarded to a screen (display) of the personal wearable device for presentation, so that the user of the personal wearable device can learn previous and current health conditions thereof. Moreover, any physiological information of the user of the personal wearable device is presented in second, minute, hour, day, week, month, quarter, and/or year, to display a chart of a physiological information trajectory over different time periods. The trajectory may be presented on the screen (display) of the smartphone or the computer, and is examined by professional healthcare personnel and used a reference when the user sees the doctor, or is provided to medical team members as a diagnostic basis. Therefore, the personal health condition can be judged immediately, thus providing a basis for personal chronic and acute disease prevention and cure and life extension.

BACKGROUND

With the continuous progress of human technologies over time, devices for detecting human body physiological information are being continuously miniaturized. Different personal wearable devices have been developed by many manufacturers. These non-invasive personal wearable devices can detect human body physiological information through the use of photoelectric technology and electromagnetic wave technology. Different detection technologies are used for detection of different body physiological information and to execute continuous dynamic detection of human body physiological information, such as, heart rhythm, blood pressure, respiratory function, blood oxygen level, stroke volume, and other human body physiological information. Among such body physiological information detected by personal wearable devices, some body physiological information cannot be detected accurately according to a result of one measurement because the result can be affected by external factors. For example, in the case of blood pressure value detection, a personal wearable device for blood pressure measurement detects blood pressure of a human body from the external of the human body in a non-invasive manner; mainly, the blood flow volume in a blood vessel under skin changes under the effect of systole and diastole, which causes a blood vessel pulse, and a blood vessel pulse value is then converted into a pressure value. However, detected blood pressure values are affected by factors such as the thickness of a subcutaneous fat tissue, obesity, age, gender, the ambient environment, weather and temperature, working conditions, emotional state, and/or angiosclerosis processes. If these blood pressure values are only used as a personal reference for the wearer, it is a pity that the present state of the art cannot improve human well-being. Methods for continuously detecting body physiological information trajectories and establishing disease prevention and cure via a personal wearable device disclosed herein may solve foregoing problem of many interference factors.

SUMMARY

The present invention relates to a method for continuously detecting body physiological information trajectories and establishing disease prevention and cure via a personal wearable device. With the continuous evolution and progress of human technologies such as the photoelectric technology, biochemical technology, information technology, communication technology, and medical technology, devices for detecting human body physiological information are being continuously miniaturized. Many different personal wearable devices have been developed by manufacturers for the purpose of personal healthcare. After years of thinking and study, the inventors believe that current photoelectric, communications, and information software programs can be combined with other medical technology to implement continuous detection of important physiological information such as heartbeat, blood oxygen, blood pressure, respiratory, and stroke volume from the external of a human body by using electromagnetic wave technologies such as an infrared technology, a Nanosecond Pulse Near-field Sensing technology, and an Ultra Wide Band (UWB) non-contact monitoring technology. However, observed and considered from another perspective, this solution is problematic in terms of continuous detection of blood pressure. The inventors of the present invention believe that the blood pressure detected from the external of the human body in a non-invasive manner is derived from a blood vessel pulse as the blood flow volume in a blood vessel in a subcutaneous tissue changes under the effect of systole and diastole, and such a periodic pulse volume curve produced in the blood vessel is indeed generated by a blood vessel-borne pressure derived from the systole and diastole. Then, by means of conversion, comparison, correction, analysis, and calculation, the pulse volume curve of the blood vessel can be converted into a blood pressure value of the blood vessel, and the systolic pressure and diastolic pressure of the heart can be found. In this non-invasive blood pressure detection manner, theoretically or practically, the systolic pressure and diastolic pressure of the blood pressure can be precisely detected. The problem is that many factors affecting the accuracy of the personal wearable device for non-invasive detection of body physiological information are ignored at present. Therefore, the inventors of the present invention intend to eliminate factors affecting the accuracy of the personal wearable device. As described above, when non-invasive personal wearable devices detect blood pressure by using an electromagnetic wave technology, the systolic pressure and diastolic pressure generated due to rhythmic heartbeats are calculated by means of conversion and comparison according to an actual pulse situation of a blood vessel pulsation waveform, and errors may be generated due to different human individuals. For example, factors such as detection time and space, age and growth, gender, body weight, psychological and physical health conditions, and whether the wearable device is worn correctly all affect the accuracy of the non-invasive detection device and the true value of the detected blood pressure. These are the disadvantages caused by actual interference factors. Moreover, in blood pressure detection executed by current wrist-type personal wearable devices sold on the market, there is no personalized design for users, and in different implementation situations of individuals, the disadvantages caused by the actual interference factors of the personal wearable devices are not eliminated. Therefore, the inventors of the present invention believe that due to the remarkable progress in various technical fields such as the photoelectric technology, communication technology, information technology, and medical technology, there should be a method that combines various technical fields to achieve a real-time and effective personal medical and health management mode. Based on the description above, the current wrist-type personal wearable device still has the disadvantages caused by actual interference factors. The inventors of the present invention update a current body physiological information detection method of the wrist-type personal wearable device, and in this way, a correct blood pressure value of a human body in a real situation can be accurately obtained, the personal wearable device can be further simplified, and the disadvantage caused by actual interference factors can also be eliminated. The updated method is described as follows: after continuously detecting a periodic pulse volume curve of body physiological information, the wrist-type personal wearable device directly transmits the periodic pulse volume curve to a smartphone or computer of the user in a wireless manner via Bluetooth, and the periodic pulse volume curve is then forwarded to a remote medical data center for storage and processing. In this case, program application software of the medical data center cannot directly interpret information about the periodic pulse volume curve, and needs to obtain numeral data of body physiological information of the wearer. Therefore, the blood pressure of the wearer is measured. The user of the wearable device can ask professional healthcare personnel to measure the blood pressure by using an additional government approved device of the same type and record measured numeral data. After the measurement is carried out for several times and measured blood pressure data is recorded, the user of the wearable device can sequentially enter into the smartphone or computer of the user the blood pressure data of the body physiological information acquired through several measurements; the blood pressure data is then transmitted to the remote medical data center for storage and processing. In this case, the medical data center stores two different types of body physiological information: continuous periodic pulse volume curves and blood pressure numeral data measured at different moments in a same period of time or measured in different periods of time. Upon receiving the two different types of body physiological information, the software program of the medical data center automatically performs storage, conversion, comparison, correction, analysis, calculation and processing, and then converts the continuous periodic pulse volume curves into readable numeral data and stores the readable numeral data. The numeral data obtained by means of conversion is correct human body blood pressure values accurately acquired specific to the individual in a real situation. According to the above description, one feature of the present invention lies in that numeral blood pressure values of the user and detected periodic pulse volume curves of the blood vessel of the user are used to calculate the systolic pressure and diastolic pressure of the blood pressure by means of conversion, comparison, correction, and analysis. In addition, if the user wants to observe and read blood pressure data of current body physiological information, the user can click on a touch screen (display) of the wrist-type personal wearable device; the click input is forwarded to the software of the remote medical data center through the smartphone or computer of the user; next, the blood pressure data of the body physiological information is output from the medical data center, and transmitted in a reverse order to the screen (display) of the smartphone or computer of the user and to the touch screen (display) of the wrist-type of the personal wearable device for display. Especially, temporal trajectory charts of periodic physiological information are presented on the screen (display) of the smartphone or computer of the user, and different trajectory charts of periodic physiological information can be clicked.

According to the description above, the software program of the medical data center receives two different types of body physiological information, continuous periodic pulse volume curves, and blood pressure numeral data measured at different moments in a same period of time or measured in different periods of time. The software program of the medical data center adopts the following processing manner: processing the systolic pressure and diastolic pressure in the blood pressure separately. As for the systolic pressure, among numeral data in the same period of time, the systolic pressure is a value of a highest point of the periodic pulse volume curve in the same period of time, and then the value of the highest point of the pulse volume curve and the numeral systolic pressure are subject to conversion, comparison, correction, analysis and calculation. As for the diastolic pressure, in the same period of time, after the highest point of the periodic pulse volume curve, the pulse volume curve goes downwards, and the slope keeps changing during the downward movement. A value of the pulse volume curve at the minimum slope and the numeral diastolic pressure of the blood pressure are subject to conversion, comparison, correction, analysis and calculation. After several times of conversion, comparison, correction, analysis, calculation and processing, the numeral data acquired by means of conversion is correct human body blood pressure values accurately acquired specific to the individual in a real situation.

As shown in the description above, execution of the method for continuously detecting body physiological information trajectories and establishing disease prevention and cure via a personal wearable device includes three parts: (I) a personal wearable device; (II) a smartphone or a computer; and (III) a medical data center, and the method can be executed only after mutual communication links are established among the three parts. The method uses a special-purpose personal wearable device for each unique user, and belongs to the typical personalized medical scope. Steps separately executed by the three parts above are described in detail below: 1. during execution, a user downloads an application software program of the medical data center from the Internet by using the smartphone or the computer, and forwards the application software program to the personal wearable device via a communication link;

2. basic personal information of the user (including name, date of birth, and ID card number), basic information of the personal wearable device (including device ID, manufacturer, date of manufacture, and model), basic information of the smartphone or computer (including mobile phone or computer ID, manufacturer, date of manufacture, and model), and the mutual communication links among the personal wearable device, the smartphone or computer, and the medical data center are entered into the application software downloaded to the smartphone or computer. Meanwhile, required information is transmitted to the personal wearable device and the medical data center;

3. the user of the personal wearable device can wear the device, and can activate the personal wearable device; a periodic pulse volume curve of continuously detected body physiological information is directly transmitted, in the form of encapsulated packets, to the smartphone or computer via a Bluetooth communication link, and then the periodic pulse volume curve detected by the device is transmitted, by means of remote wireless transmission, to the remote medical data center for storage and processing; in this example, a software program in the medical data center has not yet converted continuous periodic pulse volume curve information into numeral data information; numeral data of body physiological information of the user of the personal wearable device can be further acquired to serve as a basic information for conversion, comparison, and correction;

4. initial data conversion, comparison, and correction are executed, and the user of the personal wearable device can ask professional healthcare personnel to measure the body physiological information by using an additional government approved device of the same type and record measured numeral data; after the measurement is carried out for several times and measured numeral data is recorded, the user of the wearable device can sequentially enter, into the smartphone or computer the numeral data of the body physiological information acquired through several times of measurement; the numeral data is then transmitted to the remote medical data center for storage and processing;

5. the medical data center stores two different types of personal body physiological information of the user of the device: periodic pulse volume curve data of continuous personal body physiological information, and numeral data of multiple groups of personal body physiological information;

6. after automatically executing storage, conversion, comparison, correction, analysis, calculation, and processing on the periodic pulse volume curve data of continuous body physiological information and the numeral data of multiple groups of body physiological information that are in the same period of time, the software program of the medical data center converts the continuous periodic pulse volume curve data into readable numeral data and stores the readable numeral data; at this moment, the method of the present invention can effectively execute accurate body physiological information numeral data of the human body in a real situation;

7. the software program of the medical data center directly converts the continuous periodic pulse volume curve data into numeral data according to the previous step, and stores the numeral data in the medical data center; when needing to observe the body physiological information, the user of the wearable device may observe the body physiological information on the screen (display) of the wearable device and the screen (display) of the smartphone or computer of the user;

8. the software program of the medical data center provides a 24-hour prompt and alarm service for an abnormity in the body physiological information and improper wearing of the device by the user, and also provide data for regular or irregular data comparison and correction; the software program of the media data center can further serve to provide trajectory data of personal body physiological information at any time, to make sure that a method for prevention and cure of chronic or acute diseases is constructed.

In addition, the method for continuously detecting body physiological information trajectories and establishing disease prevention and cure via a personal wearable device comprises of three parts: (I) a personal wearable device; (II) a smartphone or a computer; and (III) a medical data center, and the three parts comprises the following features and execute the following tasks.

As for the personal wearable device: 1. the device executes continuous detection of a periodic pulse volume curve of body physiological information, where the pulse volume curve is not displayed on the screen (display); 2. the periodic pulse volume curve of the body physiological information continuously detected by the device is transmitted, in the form of encapsulated packets, to the smartphone or computer of the user of the device by means of Bluetooth transmission; 3. the periodic pulse volume curve of the body physiological information continuously detected by the device is not transformed into numeral data by means of conversion, comparison and calculation in the device or displayed on the screen (display); 4. numeral data seen on the screen (display) of the device is processed numeral data output from the medical data center; 5. round keys at the upper part of the touch screen (display) of the device are state keys, and the user may select a life state from a sitting state key, a standing state key, a walking state key, a working state key, a sporting state key, a dining state key, a sleeping state key, and other state keys according to a life state of the user; the life state is transmitted to the smartphone or computer of the user via Bluetooth, and then forwarded to the medical data center to inform the medical data center of the life state; in this way, the user of the device can learn changes in various physiological information of the body according to life states of the user; 6. round keys at the lower part of the touch screen (display) of the device are function keys, and the user may click on the touch screen (display) to select functions related to various physiological information of the body, for example: blood pressure value, blood oxygen level, heart rate, heart rhythm, respiratory, body weight, stroke volume, and other physiological information. As the technology advances and detection items for body physiological information increase, numeral data items of the body physiological information can be modified through downloading updated application software; 7. the device receives, by means of Bluetooth, numeral data and prompt information transferred by the smartphone or computer, and receives the downloaded application software, basic personal information and communication links.

As for the smartphone or computer: 1. the smartphone or computer downloads the application software of the remote medical data center from the Internet, receives the basic personal information, the ID, manufacturer, date of manufacture, and model of the personal wearable device, the ID, manufacturer, date of manufacture, and model of the of the smartphone or computer, and/or the mutual communication links into the application software, and at the same time transmits the basic personal information, the ID, manufacturer, date of manufacture, and model of the personal wearable device, the ID, manufacturer, date of manufacture, and model of the of the smartphone or computer, and the mutual communication links to the personal wearable device and the medical data center; 2. the smartphone or computer receives the periodic pulse volume curve of the body physiological information continuously detected by the personal wearable device, and forwards the periodic pulse volume curve to the remote medical data center; 3. the smartphone or computer receives the periodic pulse volume curve of the body physiological information continuously detected by the personal wearable device, and receives the body physiological information of the user of the device measured by the professional healthcare personnel using the government approved device of the same type, and transmits the two types of physiological information expressed in different forms, that is, the periodic pulse volume curve data of the body physiological information continuously detected by the device and the numeral data measured by the professional healthcare personnel using the device of the same type, to the remote medical data center for initial conversion, comparison and correction and also for regular and irregular conversion, comparison and correction; 4. the smartphone or computer receives an input the user of the personal wearable device, and forwards the input to the medical data center; 5. the smartphone or computer receives body physiological information numeral data output by the remote medical data center, displays the numeral data on the screen (display) of the smartphone or computer screen, and forwards the numeral data to the screen (display) of the personal wearable device for display; 6. the smartphone or computer receives physiological information trajectories over different time periods output by the medical data center, where the physiological information trajectories are on the basis of second, minute, hour, day, week, month, quarter, and/or year, and displays the physiological information trajectories on the screen (display) of the smartphone or computer of the wearer, which can be provided as a reference for medical team members to observe current body physiological information or backtrack changes in the body physiological information when the user sees the doctor; 7. the smartphone or computer executes the latest entered data and data correction, and transmits the body physiological information numeral data to the medical data center so that the numeral data is used as a basis for regular correction, and subsequently transmits numeral data to the personal wearable device.

As for the medical data center: 1. the application software in the medical data center provides output to the user of the personal wearable device; 2. the medical data center receives all personal information of the wearer forwarded by the smartphone or computer, and the periodic pulse volume curve of the body physiological information continuously detected by the wearable device; 3. the medical data center receives numeral data, which is entered into the smartphone or computer, acquired in multiple times of measurement performed by the professional healthcare personnel using the device of the same type, continuously receives the periodic pulse volume curve of the body physiological information, and performs initial or regular and irregular conversion, comparison, correction and calculation on the two pieces of physiological information within the same period of time but displayed in different forms; 4. the software of the medical data center automatically executes the storage, conversion, comparison, correction, analysis, calculation, and processing of the body physiological information, converts the continuous periodic pulse volume curve into readable numeral data, and stores and processes the readable numeral data; meanwhile, the software of the medical data center can provide many users of personal wearable devices with a service of continuously detecting body physiological information; 5. the medical data center executes the input transmitted from the smartphone or computer; 6. the medical data center automatically provides a prompt indicating whether the user of the personal wearable device correctly wears the wearable device; 7. the medical data center automatically informs that the body physiological information of the user of the personal wearable device deviates from a normal value or becomes abnormal suddenly, to facilitate in-time emergency medical intervention.

DETAILED DESCRIPTION

Figure 1:
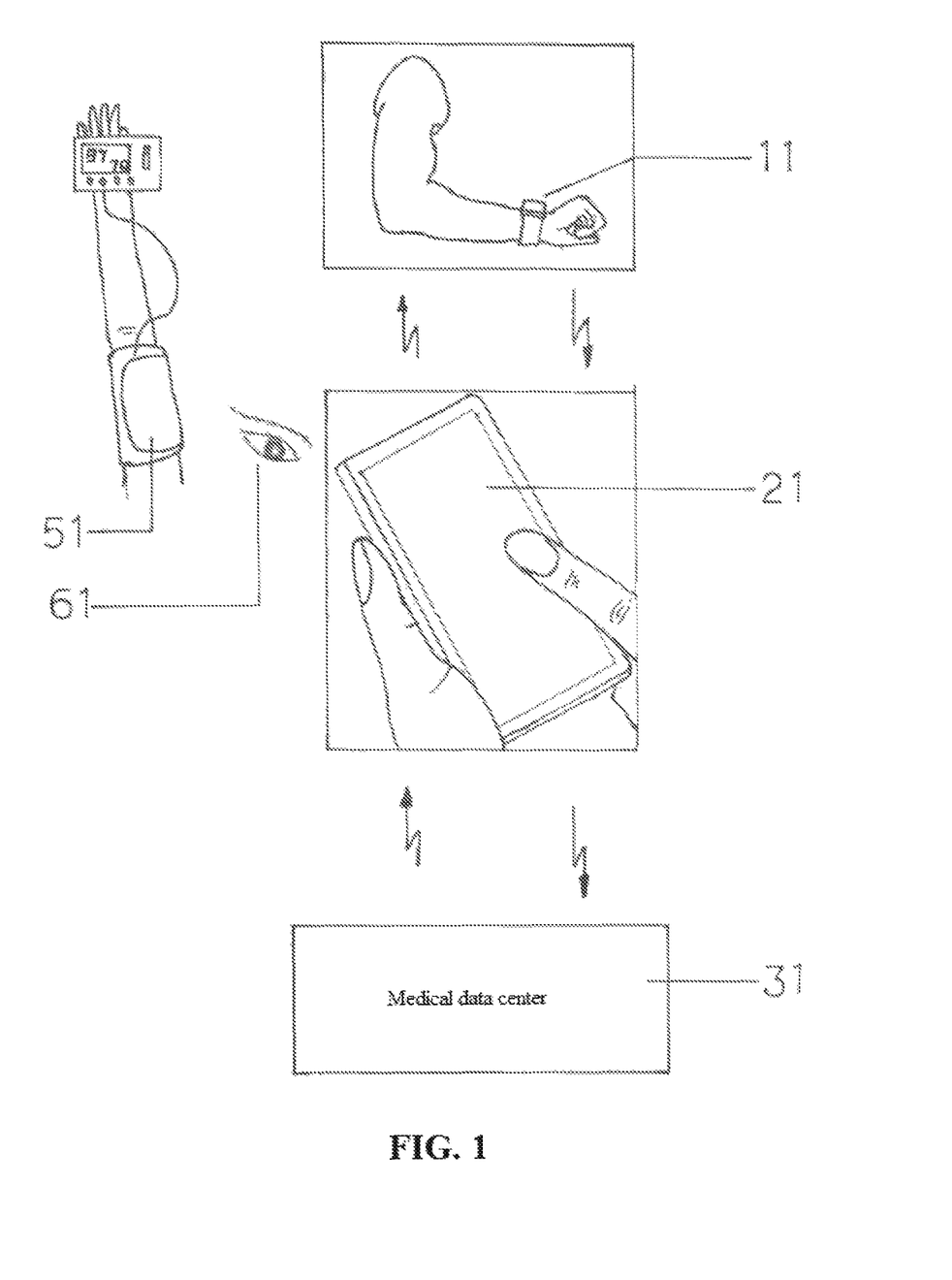
FIG. 1 is a diagram illustrating initial and regular and irregular correction of a wrist-type personal wearable device for blood pressure detection according to an embodiment of the present invention.

The present invention provides a method for continuously detecting body physiological information trajectories and establishing disease prevention and cure via a personal wearable device. As there are different types of physiological information related to human body anatomy, in most cases, physiological information of the body is detected by means of electromagnetic waves in a non-invasive manner at present. The inventors of the present invention understand that anatomy of every individual is unique, and therefore, the different body conditions of each person should be considered during detection of some body physiological information, and detection values are actually affected by interference factors. Now, a personal wearable device for blood pressure detection is used as an example. In addition, personal wearable devices are classified into many types depending on where they are worn, for example, locations such as the head, breast, and wrist. An implementation example currently used by the inventors of the present invention is a wrist-type personal wearable device for blood pressure detection. The method of the present invention is described with reference to the schematic diagrams of one of the embodiments, and is described in further detail through the architecture and operation manner of the method of the present invention; in this way, the method of the present invention can be further understood. Details are described as follows:

FIG. 1 is a diagram illustrating initial and regular and irregular correction of a wrist-type personal wearable device for blood pressure detection according to an embodiment of the present invention. This diagram comprises of three blocks, which represents a wrist-type personal wearable device 11 for blood pressure detection, a smartphone or computer 21, and a medical data center 31 respectively. The three blocks are shown with arrows representing reception and transmission of information. If a user wants to activate the wrist-type personal wearable device 11 for blood pressure detection, the user first needs to connect to the Internet by using an enter key of the smartphone or computer 21 and download an application software program of the medical data center 31. Then the smartphone or computer 21 obtains the application software program, basic personal information of the user, the ID, manufacturer, date of manufacture, and model of the wrist-type personal wearable device 11 for blood pressure detection, the ID, manufacturer, date of manufacture, and model of the smartphone or computer 21, and/or mutual communication links are entered as input to the application software.

Next, the required data is transmitted to the wrist-type personal wearable device 11 for blood pressure detection and the medical data center 31 at the same time to establish the communication connection. In this case, the user can start the wrist-type personal wearable device 11 for blood pressure detection, and transmit a periodic pulse volume curve of continuously detected body physiological information to the smartphone or computer 21 by means of Bluetooth short distance wireless transmission, and then the periodic pulse volume curve is transmitted to the medical data center 31 by means of long distance wireless transmission. Therefore, wearing the wrist-type personal wearable device 11 for blood pressure detection, the user begins to continuously provide the periodic pulse volume curve of the continuously detected body physiological information to the medical data center 31. Initial correction (as well as regular and irregular correction) is then executed, and the user can use an additional government approved device of the same type, e.g. a conventional blood pressure meter 51, and asks professional healthcare personnel to measure body physiological information and carry out visual observation 61, so as to record measured numeral data; after the measurement is performed for several times and multiple pieces of measured numeral data are recorded, the user of the personal wearable device enters the numeral data of the body physiological information acquired through several times of measurement into the smartphone or computer 21, and then the numeral data is transmitted to the remote medical data center 31 for storage and processing. In this case, the medical data center 31 stores two types of body physiological information in different forms, e.g. continuous periodic pulse volume curves, and numeral data measured at different times. After automatic storage, conversion, comparison, correction, analysis, calculation and processing, a software program of the medical data center 31 converts the continuous periodic pulse volume curve into readable numeral data and stores the readable numeral data; regular correction is then executed, which has the same program as the initial correction. If the user wants to read numeral data of current body physiological information, the user can click on a touch screen (display) of the wrist-type personal wearable device 11 for blood pressure detection; the click input is then forwarded to the software of the remote medical data center 31 through the smartphone or computer 21 of the user; next, the numeral data of the body physiological information is transmitted in reverse order to the screen (display) of the smartphone or computer 21 of the user and to the touch screen (display) of the wrist-type personal wearable device 11 for blood pressure detection, and displayed thereon. Especially, a physiological information trajectory 71 (on the basis of day) in personal physiological information trajectories over different time periods (refer to FIG. 4) is presented on the screen (display) of the smartphone or computer of the user 21, where the personal physiological information trajectories are on the basis of second, minute, hour, day, week, month, quarter, and/or year. The user may click on the touch screen of the smartphone or computer 21 to select physiological information trajectories on the basis of different time units.

Figure 2:
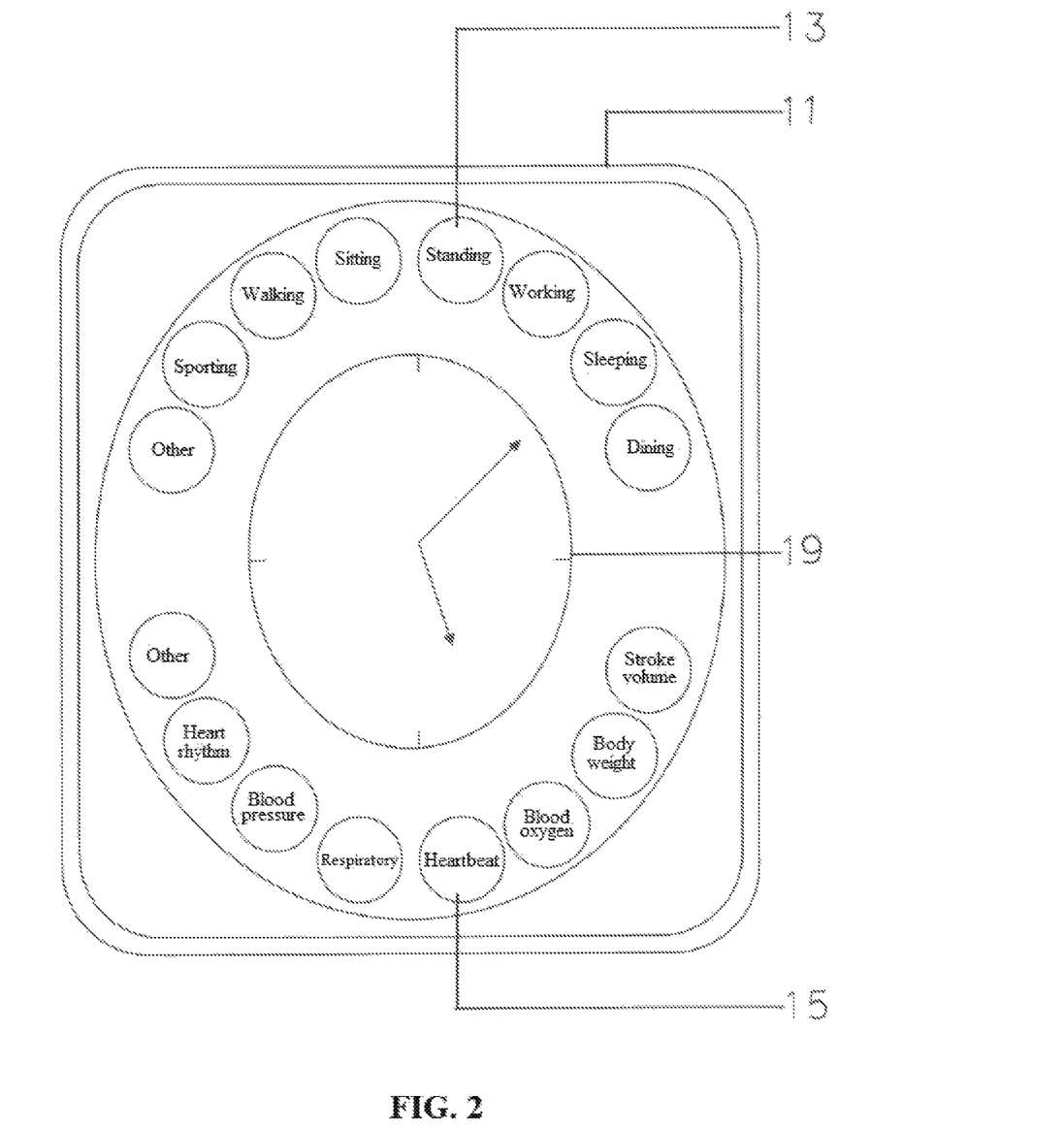
FIG. 2 is a diagram illustrating keys on a screen of a wrist-type personal wearable device for blood pressure detection according to an embodiment of the present invention.

FIG. 2 is a diagram illustrating keys on a screen of a wrist-type personal wearable device for blood pressure detection according to an embodiment of the present invention. The quadrilateral frame in the figure represents the wrist-type personal wearable device 11 for blood pressure detection. Round touch points at the lower part of the touch screen (display) are function keys 15, including: blood pressure, heartbeats, respiratory, stroke volume, body weight, blood oxygen, heart rhythm, and the like. These round touch points represent a current physiological function status of the user, and the round touch points may also be expressed in the form of text, pictures or codes. When the user uses different types of functions to detect body physiological information, the user can click different function keys, for example, the blood oxygen or heart rhythm function key. In addition, round touch points at the upper part of the touch screen (display) are state keys 13, including: a standing state key, a dining state key, a sport state key, a sitting state key, a walking state key, a sleep state key, a working state key, and other state keys. The round touch points may also be expressed in the form of text, pictures or codes, to represent a current life state of the user. When the user needs more detailed and accurate body physiological information change and body health condition, an accurate life state schedule can be entered via the state keys 13 of the wrist-type personal wearable device 11 for blood pressure detection, and the life status will be transmitted from the wrist-type personal wearable device 11 for blood pressure detection to the smartphone or computer 21 (referring to FIG. 1) via Bluetooth, and then forwarded to the software of the remote medical data center 31 (referring to FIG. 1). In this way, the software program of the medical data center 31 (referring to FIG. 1) can more accurately analyze a cause of a slight or significant change in the blood pressure of the user, and more precisely analyze the health condition of the user. It is important that the wrist-type personal wearable device 11 for blood pressure detection actively informs the remote data center of the life state, because the status of a person's life state affects all physiological information in the body, such as blood oxygen, respiratory, heartbeat, blood pressure, and heart rhythm. In addition, the central position on the touch screen (display) of the wrist-type personal wearable device 11 for blood pressure detection, a 12-hour timer 19 is provided to help grasp the schedule of life states.

Figure 3:
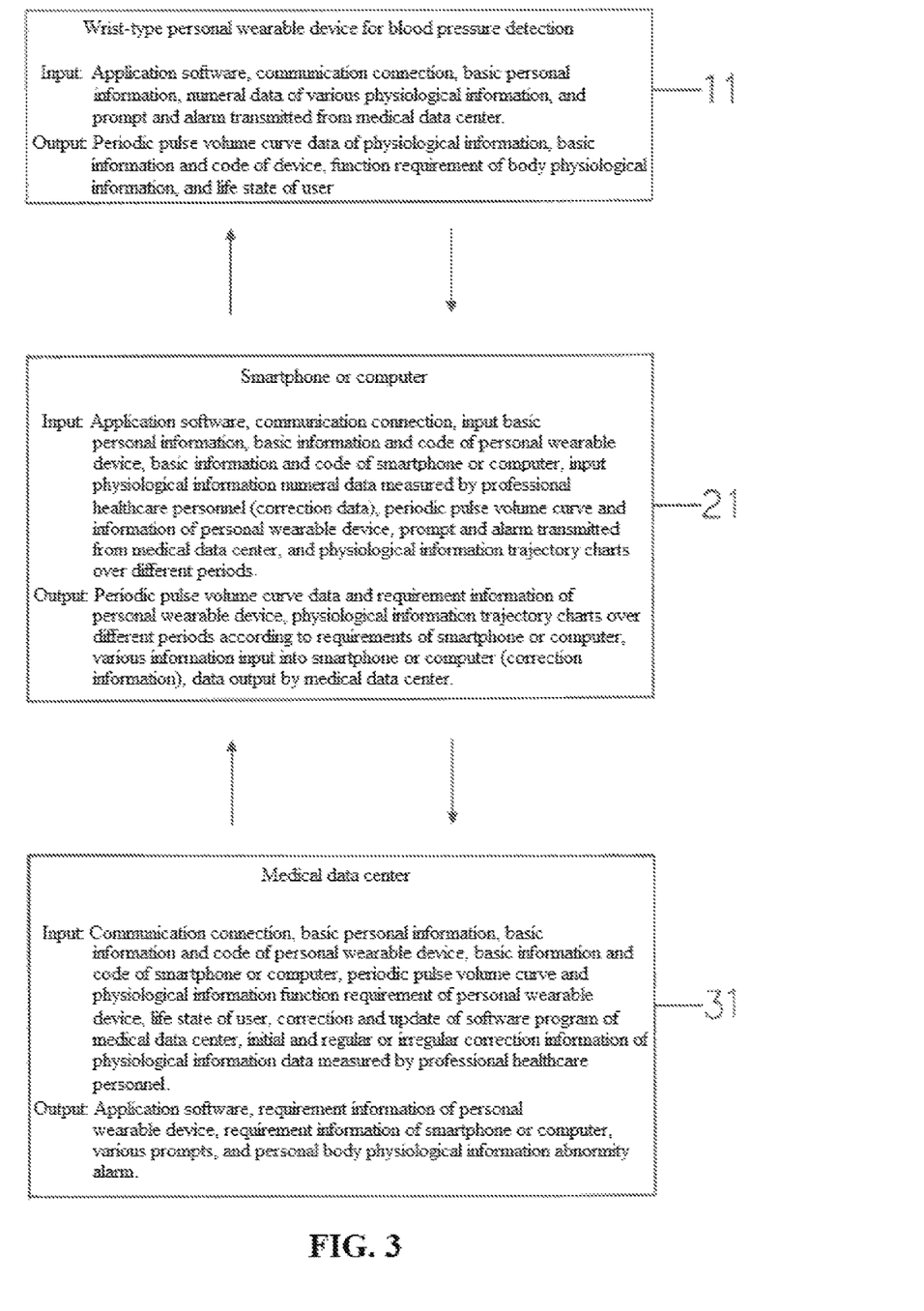
FIG. 3 is a block diagram of input and output between three parts of a method for continuously detecting body physiological information trajectories and establishing disease prevention and cure via a personal wearable device according to an embodiment of the present invention.

FIG. 3 is a block diagram of input and output of three parts of a method for continuously detecting body physiological information trajectories and establishing disease prevention and cure via a personal wearable device according to an embodiment of the present invention. FIG. 3 comprises of three blocks, which represent the wrist-type personal wearable device 11 for blood pressure detection, the smartphone or computer 21, and the medical data center 31. The three blocks are provided with arrows, representing input (reception) and output (transmission) of information; as can be clearly seen from the figure, the three parts execute different tasks. The inventors of the present invention incorporates a known blood pressure detection device, which does not allow users to perform correction specific to their bodies, within the wrist-type personal wearable device 11 for blood pressure detection which is suitable for use by any person and allows users to perform correction, which can eliminate interference factors such as age and growth, gender, climate, working, body weight, psychological and physical health states, and whether the wearable device is correctly worn, and can accurately detect blood pressure.

Figure 4:
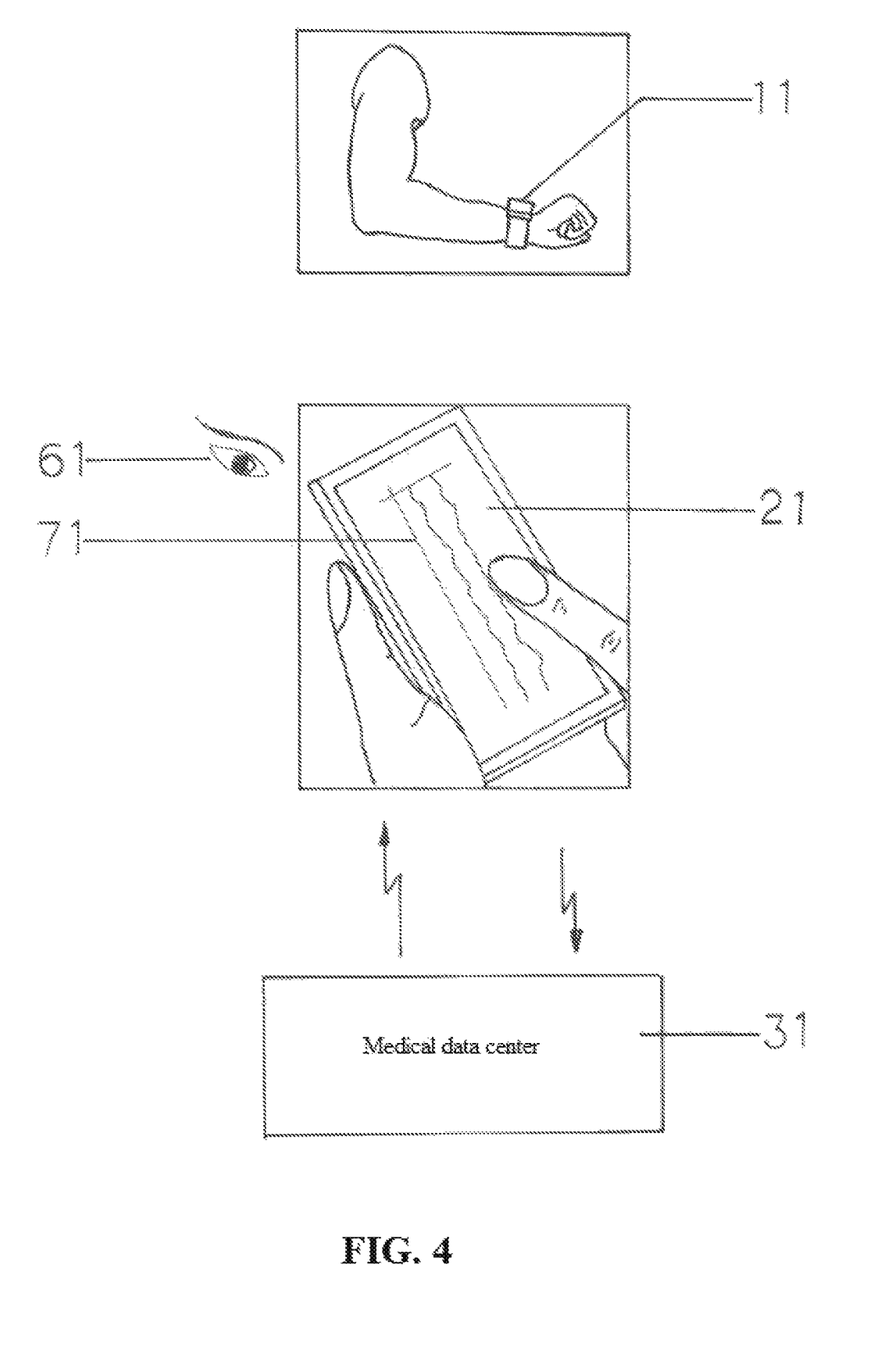
FIG. 4 is a schematic diagram illustrating that a wrist-type personal wearable device for blood pressure detection continuously detects body physiological information continuously and provides a trajectory for observation by professional healthcare personnel according to an embodiment of the present invention.

FIG. 4 is a schematic diagram illustrating that a wrist-type personal wearable device for blood pressure detection continuously detects body physiological information and provides a trajectory to be observed by professional healthcare personnel according to an embodiment of the present invention. This figure comprises of three blocks, which represent the wrist-type personal wearable device 11 for blood pressure detection, the smartphone or computer 21, and the medical data center 31. Among the three blocks, arrows pointing to different directions are only provided between two blocks, representing that reception and output of information that occurs between the smartphone or computer 21 and the medical data center 31, and representing that the user can acquire a physiological information trajectory 71 (on the basis of day) from the medical data center 31, where the trajectory 71 is provided for the user for observation 61 as well as irregular tracing, backtracking or learning, or the trajectory 71 is provided for medical team members so that they carry out observation 61 on current blood pressure or backtrack blood pressure changes and use the blood pressure changes as a reference when the user sees the doctor.

Figure 5:
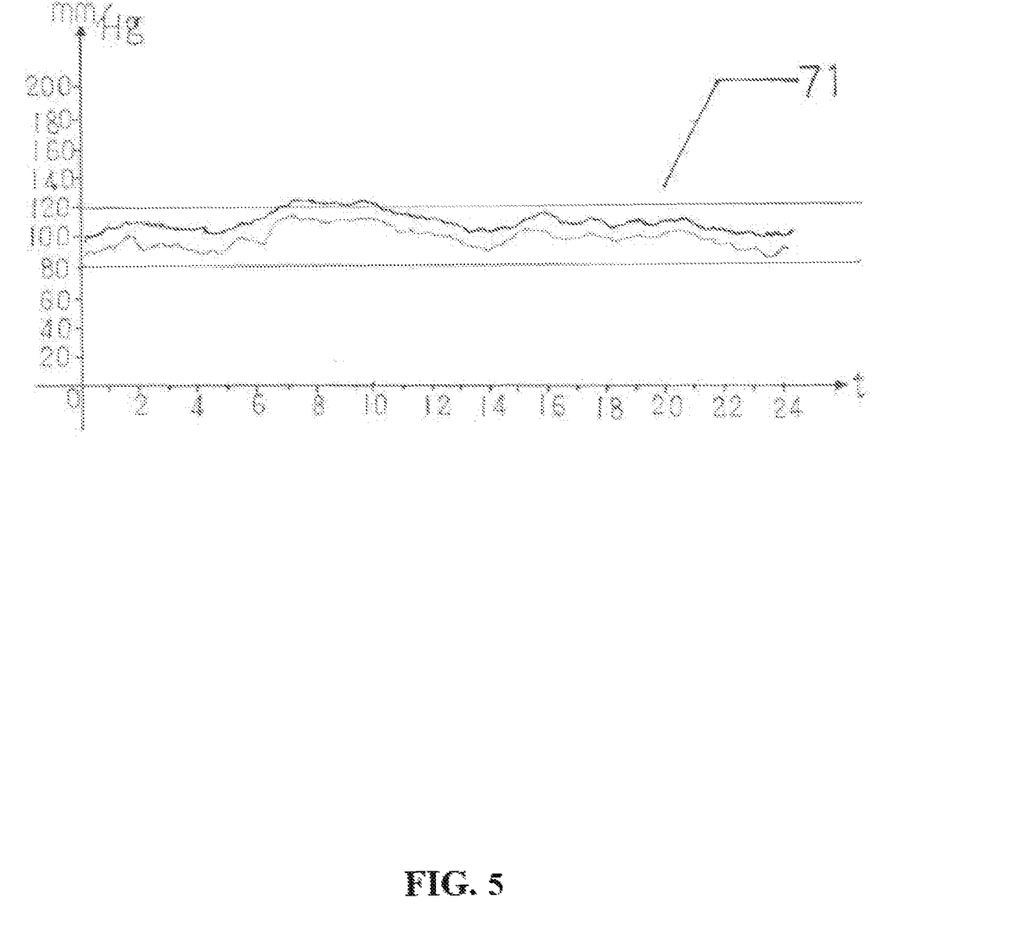
FIG. 5 is a trajectory chart of body physiological information (on the basis of day) continuously detected by a wrist-type personal wearable device for blood pressure detection according to an embodiment of the present invention.

FIG. 5 is a trajectory chart of body physiological information (on the basis of day) continuously detected by a wrist-type personal wearable device for blood pressure detection according to an embodiment of the present invention. This chart shows a trajectory 71 of body physiological information on the basis of day, where the horizontal axis of the chart is a time axis represented by t, and the vertical axis of the chart is a pressure axis represented by mm/Hg. The horizontal axis of the chart, namely, the time axis, may be a personal physiological information trajectory over different time periods, which is set on the basis of second, minute, hour, day, week, month, quarter, and/or year. The vertical axis of the chart represents blood pressure values, where the fluctuating thick line above represents the systolic pressure, and the fluctuating thin line below represents the diastolic pressure. It can be observed from the chart that: 22:00 to 24:00 and 0:00 to 6:00 are sleep time, and the blood pressure value in this period of time is relatively low; in 6:00 to 12:00 and 14:00 to 20:00, the user is in a working or walking state, and therefore the blood pressure value is relatively high.

MEANINGS OF REFERENCE SIGNS IN THE FIGURES

11 Wrist-type personal wearable device for blood pressure detection
13 State key
15 Function key
19 12-hour timer
21 Smartphone or computer
31 Medical data center
51 Conventional blood pressure meter (government approved device of the same type)
61 Observation
71 Physiological information trajectory on a daily basis

What is claimed is:

1. A method for continuously detecting body physiological information trajectories via a personal wearable device, a smartphone or a computer, and a medical data center, the method comprising:
   executing an application software program that is configured to communicate with the medical data center on a personal wearable device;
   sending information for blood pressure detection from the smartphone or the computer to the personal wearable device and the medical data center;
   detecting first body physiological information for generating a pulse volume curve by the personal wearable device;
   transmitting data of the pulse volume curve of the first body physiological information by the personal wearable device through the smartphone or computer to the medical data center;
   measuring second body physiological information by using an additional device of a same type more than once;
   receiving numerical data of the second body physiological information by the smartphone or computer;
   transmitting the numerical data from the smartphone or computer to the medical data center and to the personal wearable device;
   storing the data of the pulse volume curve of the first body physiological information and the numerical data from the second body physiological information at the medical data center;
   processing, by the medical data center, the data of the pulse volume curve of the first body physiological information and the numerical data of the second body physiological information wherein processing the data of the pulse volume curve of the first body physiological information includes converting the data of the pulse volume curve into readable numerical data and storing the readable numerical data;

displaying the first body physiological information on a screen of the personal wearable device or a screen of the smartphone or the computer, wherein displaying the first body physiological information on the screen of the personal wearable device or the screen of the smartphone or the computer includes displaying a physiological information trajectory on the screen of the smartphone or the computer, the physiological information trajectory is provided as a reference for medical team members to observe current first body physiological information or backtrack changes in the first body physiological information;

providing 24-hour alarm service, data of a physiological information trajectory based on third body physiological information or data for regular or irregular data comparison and correction whenever the medical data center detects an abnormality in the first body physiological information or improper wearing of the device by the user; and receiving the data of the physiological information trajectory by the smartphone or the computer over different time periods from the medical data center, wherein receiving numerical data of the second body physiological information into the smartphone or the computer includes receiving entries of latest data and data correction based on the numerical data of the second body physiological information.

2. The method according to claim 1, further comprising:

selecting a life state of the user on said personal wearable device, where round keys at the upper part of the touch screen of the device are state keys, and the user may select the life state from a sitting state key, a standing state key, a walking state key, a working state key, a sporting state key, a dining state key, a sleeping state key, or other state keys according to the life state of the user;

transmitting to the medical data center through the smartphone or computer the life state of the user via Bluetooth, and then forwarded to the medical data center to inform the medical data center of the life state.

3. The method according to claim 1, wherein the medical data center is configured to automatically provide a prompt indication whether the user of the personal wearable device correctly wears the wearable device, and automatically inform that the body physiological information of the user of the personal wearable device deviates from a normal value or becomes abnormal suddenly, to facilitate in-time emergency medical intervention.

* * * * *